(12) United States Patent
Sun et al.

(10) Patent No.: US 7,696,228 B2
(45) Date of Patent: Apr. 13, 2010

(54) ORAL PREPARATION OF DYCLONINE HYDROCHLORIDE

(75) Inventors: Tianjiang Sun, Taizhou (CN); Xiaohong Gu, Taizhou (CN); Hongguo Lu, Taizhou (CN); Min Chen, Taizhou (CN)

(73) Assignee: Yangtze River Pharmaceutical (Group) Co., Ltd., Taizhou (CN)

( * ) Notice: Subject to any disclaimer, the term of this patent is extended or adjusted under 35 U.S.C. 154(b) by 154 days.

(21) Appl. No.: 11/914,681

(22) PCT Filed: Jan. 13, 2006

(86) PCT No.: PCT/CN2006/000048
§ 371 (c)(1),
(2), (4) Date: Nov. 16, 2007

(87) PCT Pub. No.: WO2006/122462
PCT Pub. Date: Nov. 23, 2006

(65) Prior Publication Data
US 2008/0200506 A1     Aug. 21, 2008

(30) Foreign Application Priority Data
May 16, 2005    (CN) .......................... 2005 1 0040093

(51) Int. Cl.
*A61K 31/4453*    (2006.01)
(52) U.S. Cl. ..................................... 514/317
(58) Field of Classification Search ........................ None
See application file for complete search history.

(56) References Cited
U.S. PATENT DOCUMENTS
5,814,659 A * 9/1998 Elden .......................... 514/452

OTHER PUBLICATIONS

International Search Report dated Apr. 20, 2006 w/English translation (Four (4) pages).
Lu Zhu-ying, "The Research of Local Analgesic Antifoam Agents in Fibergastroscope Examination", Chin Pharm J., (Dec. 31, 1997), vol. 32, No. 12, pp. 749-750.
Yang Li et al., "A Study on the Preparation of Dyclonine Hydrochloride Gels", Journal of Sheyang Pharmaceutical University (May 31, 2000), vol. 17, No. 3, pp. 174-175, 187.
Xing Shi'an et al., "Preparation of Dyclonine Hydrochloride Gel", China Pharmacist 2003, vol. 6, No. 7, pp. 421-422.

* cited by examiner

*Primary Examiner*—Phyllis G. Spivack
(74) *Attorney, Agent, or Firm*—Crowell & Moring LLP

(57) ABSTRACT

The present invention discloses an oral preparation of dyclonine hydrochloride for the endoscopic examination in upper gastrointestinal tract, which has the effects of anesthetization and lubrication, and an oral preparation comprising dyclonine hydrochloride that has the advantages of avoiding foam in the body cavity, preventing vomiting, and offering a clear view. The preparation of the present invention comprises, as main ingredients, 0.2%-3% weight percent of dyclonine hydrochloride, 1%-12% weight percent of polyvinyl alcohol, 1%-10% volume percent of glycerin, 1%-10% volume percent of a defoaming agent, and a balance of a pharmaceutically acceptable adjuvant. The viscosity of the preparation is in a range of 30 to 300 mpa·s and the pH value is in a range of 2.0 to 8.0.

20 Claims, No Drawings

ORAL PREPARATION OF DYCLONINE HYDROCHLORIDE

TECHNICAL FIELD

The present invention relates to an oral preparation of dyclonine hydrochloride used for the endoscope examination in upper gastrointestinal tract, which have the effects of anaesthetization and lubrication.

TECHNOLOGY BACKGROUND

Currently, a barium meal or Lidocaine Hydrochloride Mucilage is generally used when the endoscope examination in alimentary tract is performed clinically. While the barium meal is used for the endoscope examination in alimentary tract, patients are quite painful. Additionally the view is unclear, it is inconvenient for the physician to operate, which would cause a prolonged operation and increased pain of the patients. While Lidocaine Hydrochloride Mucilage, a local anesthetic, is used for the endoscope examination in upper gastrointestinal tract, lidocaine hydrochloride has a surface anaesthetization effect, alleviating the pain of the patients. However, Lidocaine Hydrochloride Mucilage has no effect of lubrication, which could not facilitate the inserting of an endoscope, avoid the foam in the body cavity, prevent vomit, or offer a clear view, which causes inconvenience in its clinical use. Therefore, there is a need for a preparation used for the clinical endoscope examination in alimentary tract, which should have not only an anaesthetization effect on the surface of the mucous membrane but also a lubrication effect, facilitate the inserting of an endoscope, avoid the foam in the body cavity, prevents vomit, and offers a clear view.

SUMMARY OF THE INVENTION

The object of the present invention is to provide an oral preparation of dyclonine hydrochloride that is practical, convenient and reliable in the clinical endoscope examination in alimentary tract, which has an anaesthetic effect on the surface of the mucous membrane and also a lubrication effect, and can avoid the foam in the body cavity and prevent vomit so that a clear view can be obtained for a convenient examination.

For the above object, the preparation of the present invention comprises, as main ingredients, 0.2%-3% weight percent of dyclonine hydrochloride, 1%-12% weight percent of polyvinyl alcohol, 1%-10% volume percent of glycerin, 1%-10% volume percent of a defoaming agent, and a balance of a pharmaceutically acceptable adjuvant.

Preferably, the main ingredients in the preparation of the present invention are the following: 0.5%-1.5% weight percent of the dyclonine hydrochloride, 3%-8% weight percent of the polyvinyl alcohol, 2%-5% volume percent of the glycerin, 2%-5% volume percent of the defoaming agent, and the balance of a pharmaceutically acceptable adjuvant.

The preparation of the present invention may be a gel, solution, or syrup.

The preparation may have a viscosity in the range of 30 to 300 mpa·s, preferably 50 to 150 mpa·s, and a pH value in the range of 2.0 to 8.0, preferably 2.3 to 5.0.

The active ingredient of the present invention is dyclonine hydrochloride, which is the hydrochlorate of a local anesthetic dyclonine. This preparation can disrupt the conduction of various nerve impulses and stimulus, inhibit tactile sensation, baresthesia and pain sensation, and have analgesic, relieving itching and sterilizing effects on skin. This preparation has a strong penetrability, and it can be absorbed through the skin and mucous membrane. It can act rapidly and permanently. Its potency and duration are similar to that of Procaine. It is lower toxic and does not cause miosis or mydriasis when dropped in the conjunctiva. This preparation has no cross-allergic reaction with other local anesthetics. Adjuvants used in the preparation of the present invention mainly include polyvinyl alcohol, glycerin, a defoaming agent, a preservative, a correctant, a pH adjusting agent, a diluent agent and the like.

The polyvinyl alcohol in the preparation is a thickening agent, and generally its content is in the range of 1% to 12%. It can improve the viscosity of the preparation to a suitable range, thereby delaying the retention time of the preparation on the mucous membrane surface and prolonging the action time of its local anaesthetization.

The glycerin in the preparation generally has a content in the range of 1% to 10% volume percent. It can improve the preparation the effects of lubrication and preventing vomit, facilitating the inserting of the endoscope. Furthermore, it may also prevent the boiled aqueous solution of the polyvinyl alcohol from forming a membrane and agglomeration when cooled, so it would facilitate the formulation of the preparation.

The defoaming agent in the preparation, generally, may be a PPE defoaming agent for a medical use, a polyoxyethylene polyoxypropylene ether, or any of other defoaming agents for medical use or food additives, such as GPE, BAPE, MPE and the like. The content of the defoaming agent is generally in the range of 1% to 10% volume percent. It can provide the preparation the defoaming effect to avoid the foam in the body cavity and offer a clear view.

The dyclonine hydrochloride mucilage preparation is a mucilage preparation comprising dyclonine hydrochloride, polyvinyl alcohol, glycerin and a defoaming agent. It has not only the effect of surface anaesthetization on the mucous membrane, but also suitable viscosity to delay the retention time of the preparation on the mucous membrane surface and prolong the action time of local anaesthetization. It also has the effects of lubrication, defoaming and preventing vomit to facilitate the inserting of the endoscope and offer a clear view. As a result, this preparation can be used widely for endoscope examinations in various body cavities, especially for endoscope examination in upper gastrointestinal tract, in which it can provide anaesthetization, lubrication and preventing vomit effects, and also avoid the foam in the body cavity, offering a clear view.

As a pharmaceutically acceptable adjuvant of the present invention, a preservative, a correctant, a pH adjusting agent, or the like, may be selected from any of the related products listed in pharmacopeia, textbooks or literatures, and its content can be regulated according to the conventional usage and dosage.

The oral preparation of dyclonine hydrochloride according to the present invention can be clinically administrated, before the endoscope examination in upper gastrointestinal tract, generally by receiving 8-10 ml in the pars laryngea pharyngis, and after a moment then swallowing slowly. In about 10-15 minutes the endoscope examination in upper gastrointestinal tract can be performed. Its usage amount can be regulated properly according to the concentration of the active ingredient of dyclonine hydrochloride and the practical situations to be performed the endoscope examination.

The results of clinical trial showed that the rate of fine function for the dyclonine hydrochloride mucilage preparation of the present invention was 93.6% on the effects of inserting the endoscope and anaesthetization and 91.8% on the effect of defoaming, the rate of the marked effect for the present invention was 74.5%, and the total effective rate was 95.5%, all of which was significantly better than the control groups. In clinical studies, no evident adverse reaction of this preparation was found.

DETAILED DESCRIPTION OF THE PREFERRED EMBODIMENTS

The examples of the oral preparation used for the endoscope examination in alimentary tract according to the present invention are listed as follows:

Example 1

Dyclonine Hydrochloride Mucilage Preparation

| | |
|---|---|
| dyclonine hydrochloride | 10 g |
| medical defoaming agent (PPE) | 40 ml |
| polyvinyl alcohol | 60 g |
| Glycerin | 20 ml |
| ethyl Hydroxybenzoate | 0.3 g |
| Stevioside | 0.75 g |
| Menthol | 0.6 g |
| citric acid | 3.25 g |
| sodium citrate | 0.75 g |
| edible essence | 5 ml |
| purified water | Suitable amount added to make the final preparation of 1000 ml |

Preparation Process

The polyvinyl alcohol was taken, added with the purified water (60% of the total in the formula), stirred and cooked. To the resulting solution, the ethyl Hydroxybenzoate and stevioside were added. After polyvinyl alcohol was dissolved completely, the glycerin was added, then let the resulting solution stand for cooling. Next, the citric acid was taken, added with an amount of hot water to dissolve, then to which the dyclonine hydrochloride was added under stirring until dissolved, and next the mixture obtained was added to the resulting solution. Then sodium citrate was taken, added with an amount of hot water to dissolve, and then, after it was dissolved, added to the above resulting solution. Then the medical defoaming agent was added to the above resulting solution. Further, the menthol was taken, dissolved in the edible essence, and added to the above resulting solution. Then the purified water was added to let the final solution up to 1000 ml, and the final solution was stirred to be homogeneous and filled to yield a final product.

Example 2

Dyclonine Hydrochloride Oral Solution Preparation

| | |
|---|---|
| Dyclonine hydrochloride | 15 g |
| defoaming agent (GPE) | 20 ml |
| Polyvinyl alcohol | 20 g |
| Glycerin | 35 ml |
| sorbic acid | 0.5 g |
| Sucrose | 80 g |
| edible essence | 10 ml |
| purified water | Suitable amount added to make the final preparation of 1000 ml |

Preparation Process

The polyvinyl alcohol was taken, added with the purified water (30% of the total in the formula), stirred and steamed. To the resulting solution, the sucrose and sorbic acid were added. After the polyvinyl alcohol was dissolved completely, the glycerin was added, and then let the resulting solution stand for cooling. Next, the dyclonine hydrochloride was taken, added with an amount of hot water, and, after it was dissolved, added to the above resulting solution. Then the defoaming agent and edible essence were added the above resulting solution. Then the purified water was added to let the final solution up to 1000 ml, and the final solution was stirred to be homogeneous and filled to yield a final product.

Example 3

Dyclonine Hydrochloride Oral Gel Preparation

| | |
|---|---|
| dyclonine hydrochloride | 2 g |
| defoaming agent (BAPE) | 10 ml |
| polyvinyl alcohol | 120 g |
| Glycerin | 100 ml |
| sodium benzoate | 2 g |
| Stevioside | 1 g |
| potassium dihydrogen phosphate | 100 g |
| edible essence | 8 ml |
| purified water | Suitable amount added to make the final preparation of 1000 ml |

Preparation Process

The polyvinyl alcohol was taken, added with the purified water (50% of the total in the formula), stirred and steamed. To the resulting solution, the sodium benzoate and stevioside were added. After the polyvinyl alcohol was dissolved completely, the glycerin was added, and then let the resulting solution stand for cooling. Next, the potassium dihydrogen phosphate was taken, added with an amount of hot water to dissolve, added with the dyclonine hydrochloride under stirring until dissolved, and then added to the above resulting solution. Then the medical defoaming agent and edible essence were added. Then the purified water was added to let the final solution up to 1000 ml, and the final solution was stirred to be homogeneous and filled to yield a final product.

Example 4

Dyclonine Hydrochloride Syrup Preparation

| | |
|---|---|
| dyclonine hydrochloride | 30 g |
| defoaming agent (MPE) | 100 ml |
| polyvinyl alcohol | 10 g |
| Glycerin | 10 ml |
| Sucrose | 450 g |
| benzoic acid | 2 g |
| edible essence | 6 ml |
| diluted hydrochloric acid | adequate amount |
| purified water | Suitable amount added to make the final preparation of 1000 ml |

Preparation Process

The polyvinyl alcohol was taken, added with the purified water (55% of the total in the formula), stirred and steamed. To the resulting solution, the sucrose and benzoic acid were added. After the polyvinyl alcohol and sucrose were dissolved completely, the glycerin was added, and then let the resulting solution stand for cooling. Next, the dyclonine hydrochloride was taken, added with an amount of hot water to dissolve, and then added to the resulting solution. The pH value of the resulting solution is adjusted to 3.0±0.2 with a proper amount of diluted hydrochloric acid, and then the defoaming agent and edible essence were added. Then the purified water was added to let the final solution up to 1000 ml, and the final solution was stirred to be homogeneous and filled to yield a final product.

The other examples with different contents can be made by modifying the formula by using conventional technique in accordance with the above-mentioned examples.

Animal Example 1

Main Pharmacodynamic Studies on the Dyclonine Hydrochloride Mucilage Preparation of the Present Invention The effect of local anaesthetization of the dyclonine hydrochloride mucilage preparation was tested by the rabbit corneal and frog skin method. The experimental results of the rabbit corneal method showed that the dyclonine hydrochloride solution and mucilage preparations had a good dosage-dependent relationship on the effect of surface anaesthetization of the rabbit cornea, and the relationship between time efficiency and quantity efficiency of the mucilage preparation was similar to that of the dyclonine hydrochloride solution preparation. The $ED_{50}$ of the mucilage preparation had no significant difference from the $ED_{50}$ of the dyclonine hydrochloride solution preparation. The experimental results of the frog skin method showed that there was significant quantity efficiency-dependent relationship for the dyclonine hydrochloride mucilage and solution preparations in a range of dosages from 0.5 to 2%. The effect of local anaesthetization of the mucilage preparation had no significant difference from that of the dyclonine hydrochloride solution preparation.

Animal Example 2

Animal Acute Toxicity Tests for the Dyclonine Hydrochloride Mucilage Preparation of the Present Invention The $LD_{50}$ and 95% confidence limit of the dyclonine hydrochloride mucilage preparation administered to mice orally was 0.21 g/kg (0.19-0.23 g/kg), which was corresponding to 126 times of the recommended clinical dosage.

The $LD_{50}$ and 95% confidence limit of the dyclonine hydrochloride mucilage preparation administered to mice via intraperitoneal injection was 0.047 g/kg (0.044-0.050 g/kg), which was corresponding to 28.2 times of the recommended clinical dosage.

The $LD_{50}$ and 95% confidence limit of the dyclonine hydrochloride mucilage preparation administered to rats orally was 0.37 g/kg (0.32-0.42 g/kg), which was corresponding to 222 times of the recommended clinical dosage.

The $LD_{50}$ of the control mucilage administered to mice orally was more than 80 ml/kg.

Animal Example 3

Mucous Membrane Irritation Tests for the Dyclonine Hydrochloride Mucilage Preparation of the Present Invention Forty healthy SD rats were selected and randomly divided into three groups as a control group, low dosage group and high dosage group, respectively, and each has half male and half female. There were eight rats in the control group, and sixteen rats in each of the low dosage group and high dosage group, respectively. The groups were administered with physiological saline, 5 ml/kg and 10 ml/kg of 1% dyclonine hydrochloride mucilage preparation respectively by a single lavage. The animals were sacrificed in various groups at 1, 2, 8 and 24 h after administered, then observed the change of the oral cavity, esophagus and gastric mucosa by naked eyes and microscope. The results showed that this preparation is safe, no evident damage was found either by naked eye observations or in microscopic examination at 1, 2, 8 and 24 h after the lavage.

Application Example 1

Clinical Trial for Endoscope Examination in Upper Gastrointestinal Tract with the Dyclonine Hydrochloride Mucilage Preparation of the Present Invention Two hundred and twenty outpatients and hospital patients were tested for the endoscope examination and treatment in upper gastrointestinal tract, in ages from 19 to 79 years old, in which 121 were male and 99 female. The patients were randomly divided into two groups by using double blind, each had 110 patients. The control drug was lidocaine hydrochloride mucilage. The results showed that the observation was performed for all of the 200 patients, and two groups were substantially same in the aspects of ages, sex and entity of the patients. The rate of fine function of the effects on inserting of the endoscope and anaesthetization for the dyclonine hydrochloride mucilage group was 93.6% (103/110), the rate of fine function of the effect on defoaming was 91.8% (101/110), which were better than 70.9% (78/110) and 49.1% (54/110) of the lidocaine hydrochloride mucilage group respectively. There was significant difference between the two groups ($P<0.05$). The rate of the marked effect was 74.5 (82/110) and the total effective rate was 95.5% (105/110) for the dyclonine hydrochloride mucilage group, which were significant better than the rate of the marked effect of 30.9% (34/110) and the total effective rate of 63.6% (70/110) for the lidocaine hydrochloride mucilage group. There was significant difference between the two groups ($P<0.05$). No evident adverse reaction of the two groups was found in the medication applications.

What we claim is:

1. A oral preparation of dyclonine hydrochloride, consisting of, as main ingredients, 0.2%-3% weight percent of dyclonine hydrochloride, 1%-12% weight percent of polyvinyl alcohol, 1%-10% volume percent of glycerin, 1%-10% volume percent of a defoaming agent, and a balance of a pharmaceutically acceptable adjuvant.

2. The preparation according to claim 1, wherein the main ingredients in the preparation are 0.5%-1.5% weight percent of the dyclonine hydrochloride, 3%-8% weight percent of polyvinyl alcohol, 2%-5% volume percent of the glycerin, 2%-5% volume percent of the defoaming agent, and the balance of a pharmaceutically acceptable adjuvant.

3. The preparation according to claim 2, wherein the defoaming agent is a defoaming agent selected from a group consisting of a medical defoaming agent and a food additive defoaming agent.

4. The preparation according to claim 3, wherein the defoaming agent is polyoxypropylene polyoxypropylene pentaerythritol ether ("PPE"), polyoxypropylene oxyethylene glycerin ether ("GPE"), polyoxyethylene polyoxypropylene propanol amine ether ("BAPE")or polyoxypropylene polyoxyethylene glycerin ether ("MPE").

5. The preparation according to claim 2, wherein the preparation is a gel, solution or syrup.

6. The preparation according to claim 2, wherein a viscosity of the preparation is in a range of 30 to 300 mpa·s and a pH value is in a range of 2.0 to 8.0.

7. The preparation according to claim 6, wherein the viscosity of the preparation is in a range of 50 to 150 mpa·s and the pH value is in a range of 2.3 and 5.0.

8. The preparation according to claim 2, wherein the pharmaceutically acceptable adjuvant is selected from a group consisting of a preservative, a correctant, a pH adjusting agent, and a diluent agent and any combination thereof.

9. The preparation according to claim 8, wherein the preservative is selected from a group consisting of ethyl hydroxybenzoate, sorbic acid, sodium benzoate and benzoic acid, and any combination thereof.

10. The preparation according to claim 8, wherein the correctant is selected from a group consisting of stevioside, menthol, edible essence, citric acid, sodium citrate and sucrose, and any combination thereof.

11. The preparation according to claim 8, wherein the diluent agent is water.

12. The preparation according to claim 1, wherein the defoaming agent is a defoaming agent selected from a group consisting of a medical defoaming agent and a food additive defoaming agent.

13. The preparation according to claim 12, wherein the defoaming agent is polyoxyethylene polyoxypropylene pentaerythritol ether ("PPE"), polyoxypropylene oxyethylene glycerin ether ("GPE"), polyoxyethylene polyoxypropylene propanol amine ether ("BAPE") or polyoxypropylene polyoxyethylene glycerin ether ("MPE").

14. The preparation according to claim 1, wherein the preparation is a gel, solution or syrup.

15. The preparation according to claim 1, wherein a viscosity of the preparation is in a range of 30 to 300 mpa·s and a pH value is in a range of 2.0 to 8.0.

16. The preparation according to claim 15, wherein the viscosity of the preparation is in a range of 50 to 150 mpa·s and the pH value is in a range of 2.3 and 5.0.

17. The preparation according to claim 1 , wherein the pharmaceutically acceptable adjuvant is selected from a group consisting of a preservative, a correctant, a pH adjusting agent and a diluent agent, and any combination thereof.

18. The preparation according to claim 17, wherein the preservative is selected from a group consisting of ethyl hydroxybenzoate, sorbic acid, sodium benzoate and benzoic acid, and any combination thereof.

19. The preparation according to claim 17, wherein the correctant is selected from a group consisting of stevioside, menthol, edible essence, citric acid, sodium citrate and sucrose, and any combination thereof.

20. The preparation according to claim 17, wherein the diluent agent is water.

\* \* \* \* \*